United States Patent
Sugawara et al.

(10) Patent No.: US 6,998,495 B2
(45) Date of Patent: Feb. 14, 2006

(54) METHOD FOR PRODUCING OPTICALLY ACTIVE 3,5-DIHYDROXYCARBOXYLIC ACID DERIVATIVE

(75) Inventors: Masanobu Sugawara, Hyogo (JP); Kenji Inoue, Hyogo (JP)

(73) Assignee: Kaneka Corporation, Kita-Ku (JP)

( * ) Notice: Subject to any disclaimer, the term of this patent is extended or adjusted under 35 U.S.C. 154(b) by 23 days.

(21) Appl. No.: 10/492,507

(22) PCT Filed: Oct. 24, 2002

(86) PCT No.: PCT/JP02/11036

§ 371 (c)(1),
(2), (4) Date: Apr. 13, 2004

(87) PCT Pub. No.: WO03/040082

PCT Pub. Date: May 15, 2003

(65) Prior Publication Data
US 2004/0254392 A1 Dec. 16, 2004

(30) Foreign Application Priority Data
Oct. 24, 2001 (JP) .............................. 2001-327019

(51) Int. Cl.
*C07C 51/36* (2006.01)
(52) U.S. Cl. ...................................... 554/145; 554/141
(58) Field of Classification Search ................ 554/141, 554/145
See application file for complete search history.

(56) References Cited

U.S. PATENT DOCUMENTS 4,739,084 A  4/1988  Takaya et al.

FOREIGN PATENT DOCUMENTS

| JP | 05-308977 | 11/1993 |
|---|---|---|
| WO | WO 92/10461 | 6/1992 |
| WO | WO 92/10503 | 6/1992 |

OTHER PUBLICATIONS

International Search Report From Corresponding International Application No. PCT/JP02/11036, Dated Mar. 4, 2003, 1 Page.

*Primary Examiner*—Deborah D. Carr
(74) *Attorney, Agent, or Firm*—Brinks Hofer Gilson & Lione

(57) ABSTRACT

A method for producing an optically active 3,5-dihydroxyhexanoic acid derivative by stereoselectively reducing an optically active 3-oxo-5-hydroxyhexanoic acid derivative is provided. The method, which requires neither an ultralow-temperature reactor, an incubator, nor protection of the 5-position hydroxy group, is simple and economical.

An optically active 3,5-dihydroxyhexanoic acid derivative is produced by asymmetrical hydrogenation of an optically active 3-oxo-5-hydroxyhexanoic acid derivative catalyzed by an $RuBr_2BINAP$ complex prepared from a ruthenium complex and a ruthenium-optically active phosphine complex, i.e., 2,2'-bisdiarylphosphino-1,1'-binaphthyl (BINAP), while using extremely inexpensive hydrogen as the reductant.

12 Claims, No Drawings

METHOD FOR PRODUCING OPTICALLY ACTIVE 3,5-DIHYDROXYCARBOXYLIC ACID DERIVATIVE

RELATED APPLICATIONS

This application is a nationalization of PCT Application No. PCT/JP02/11036 filed Oct. 24, 2002. This application claims priority from Japanese Patent Application No. 2001-327019 filed on Oct. 24, 2001.

1. Technical Field

The present invention relates to a method for producing an optically active 3,5-dihydroxyhexanoic acid derivative. In particular, it relates to a method for producing the optically active 3,5-dihydroxyhexanoic acid derivative by stereoselectively reducing a carbonyl group of an optically active 3-oxo-5-hydroxyhexanoic acid derivative.

The optically active 3,5-dihydroxyhexanoic acid derivative is suitable for use as a drug intermediate, in particular an intermediate for HMG-CoA reductase inhibitors.

2. Background Art

In producing an optically active 3,5-dihydroxyhexanoic acid derivative by stereoselectively reducing a carbonyl group of an optically active 3-oxo-5-hydroxyhexanoic acid derivative, the following methods have been conventionally employed:

(1) a method for producing an optically active 3,5,6-trihydroxyhexanoic acid derivative by stereoselectively reducing an optically active 3-oxo-5,6-dihydroxyhexanoic acid derivative in the presence of sodium borohydride and triethylborane (Japanese Unexamined Patent Application Publication No. 2-262537);

(2) a method for producing optically active 6-benzyloxy-3,5-dihydroxyhexanoic acid through asymmetric hydrogenation of 6-benzyloxy-5-tetrahydropyranyloxy-3-oxohexanoic acid tert-butyl ester catalyzed by $Ru_2Cl_4$ [BINAP]$_2$N($CH_2CH_3$), which is a ruthenium-optically active phosphine complex (Japanese Unexamined Patent Application Publication No. 6-65226);

(3) a method including asymmetric hydrogenation of 6-tert-butoxy-5-hydroxy-3-oxohexanoic acid tert-butyl ester using the same catalyst as in (2) above (Japanese Unexamined Patent Application Publication No. 2-289537);

(4) a method for producing an optically active 2,4-dihydroxyadipinic acid derivative by stereoselectively reducing an optically active 4-oxo-2-hydroxyadipinic acid derivative in the presence of sodium borohydride and triethylborane (Japanese Unexamined Patent Application Publication No. 4-69355; and (5) a method for producing an optically active 2,4-dihydroxyadipinic acid derivative by stereoselectively reducing an optically active 4-oxo-2-hydroxyadipinic acid derivative in the presence of microorganisms (Japanese Unexamined Patent Application Publication No. 5-308977).

In the methods of paragraphs (1) and (4) employing sodium borohydride, the reaction must be carried out under ultralow temperatures of about −80° C. to yield high stereoselectivity; moreover, these methods are cost-ineffective due to the use of relatively expensive reagents. The method of paragraph (5) employing microorganisms requires an incubator and treatment of reaction solutions. In the method of paragraph (2), the 5-position hydroxy is protected to yield high stereoselectivity; accordingly, introduction and extraction of protective groups are necessary. In the method of paragraph (3), the 5-position hydroxy is unprotected, but the reaction is carried out under a high hydrogen pressure of 50 kg/cm²; moreover, the reaction yield and selectivity are far from satisfactory.

SUMMARY OF INVENTION

The present invention provides a simple and cost-effective method for producing an optically active 3,5-dihydroxyhexanoic acid derivative, the method requiring neither ultralow-temperature reaction equipment, culture equipment, nor protection of the 5-position.

The present inventors have conducted extensive investigations to solve the problem of the related art and found that an optically active 3,5-dihydroxyhexanoic acid derivative can be synthesized by asymmetric hydrogenation of an optically active 3-oxo-5-hydroxyhexanoic acid derivative using inexpensive hydrogen as the reductant. The asymmetric hydrogenation is catalyzed by a ruthenium-optically active phosphine complex, in particular, a $RuBr_2BINAP$ complex prepared from optically active 2,2'-bisdiarylphosphino-1,1'-binaphthyl (BINAP) and a ruthenium complex.

In particular, the present invention provides a method for producing an optically active 3,5-dihydroxyhexanoic acid derivative represented by formula (1):

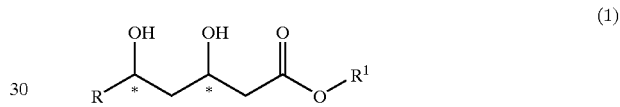

(wherein $R^1$ is $C_1$–$C_{10}$ alkyl, $C_7$–$C_{20}$ aralkyl, or $C_6$–$C_{20}$ aryl, and R is

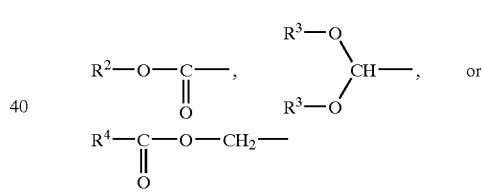

wherein $R^2$ is $C_1$–$C_{10}$ alkyl, $C_7$–$C_{20}$ aralkyl, or $C_6$–$C_{20}$ aryl; $R^3$s are each independently $C_1$–$C_{10}$ alkyl, $C_7$–$C_{20}$ aralkyl, or $C_6$–$C_{20}$ aryl, or together form $C_1$–$C_{10}$ alkylene; and $R^4$ is $C_1$–$C_{10}$ alkyl, $C_7$–$C_{20}$ aralkyl, or $C_6$–$C_{20}$ aryl), the method including a step of conducting asymmetric hydrogenation of an optically active 3-oxo-5-hydroxyhexanoic acid derivative represented by formula (2) in the presence of a ruthenium-optically active phosphine complex as a catalyst:

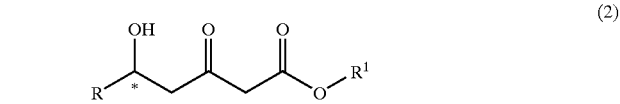

(wherein R and $R^1$ are the same as described above).

The present invention also relates to the above-described method in which the ruthenium-optically active phosphine complex is a $RuBr_2BINAP$ complex prepared from 2,2'-bisdiarylphosphino-1,1'-binaphthyl and a ruthenium complex.

The present invention also relates to the method for producing an optically active 3,5,6-trihydroxyhexanoic acid derivative represented by formula (4)

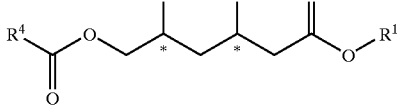
(4)

(wherein $R^1$ and $R^4$ are the same as above) through asymmetric hydrogenation of an optically active 3-oxo-5,6-dihydroxyhexanoic acid derivative represented by formula (3)

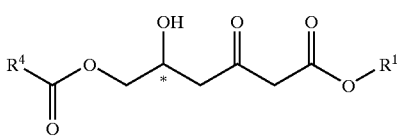
(3)

(wherein $R^1$ and $R^4$ are the same as above)

The present invention also relates to the method for producing an optically active 2,4-dihydroxyadipinic acid derivative represented by formula (6)

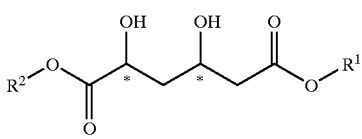
(6)

(wherein $R^1$ and $R^2$ are the same as above) through asymmetric hydrogenation of an optically active 4-oxo-2-hydroxyadipinic acid derivative represented by formula (5)

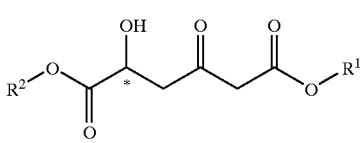
(5)

(wherein $R^1$ and $R^2$ are the same as above)

The present invention also relates to the method for producing an optically active 3,5-dihydroxyhexanoic acid derivative represented by formula (8)

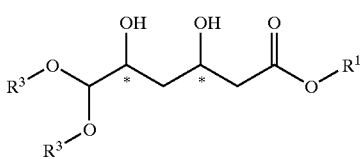
(8)

(wherein $R^1$ and $R^3$ are the same as above) through asymmetric hydrogenation of an optically active 3-oxo-5-hydroxyhexanoic acid derivative represented by formula (7)

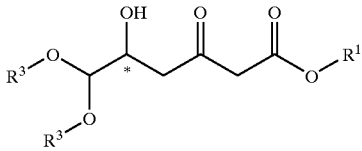
(7)

(wherein $R^1$ and $R^3$ are the same as above)

DETAILED DESCRIPTION OF THE INVENTION

The present invention will now be described in detail.

In the present invention, the optically active 3-oxo-5-hydroxyhexanoic acid derivative represented by formula (2) above is subjected to asymmetric hydrogenation to produce the 3,5-dihydroxyhexanoic acid derivative represented by formula (1) above.

In particular, the compound represented by formula (3), (5), or (7) is subjected to asymmetric hydrogenation to produce the compound represented by formula (4), (6), or (8), respectively.

In formulae (1) to (8) above, $R^1$ represents a $C_1$–$C_{10}$ alkyl group, a $C_7$–$C_{20}$ aralkyl group, or a $C_6$–$C_{20}$ aryl group. The alkyl, aralkyl, or aryl group may contain a substituent. The substituent may be any suitable one. For example, the substituent may be a hydroxy group, a $C_1$–$C_{10}$ alkyl group, a $C_1$–$C_{10}$ alkoxy group, a sulfur atom, a nitrogen atom, or an oxygen atom.

The $C_1$–$C_{10}$ alkyl group may be any suitable one. For example, the $C_1$–$C_{10}$ alkyl group may be methyl, ethyl, n-propyl, isopropyl, n-butyl, isobutyl, t-butyl, n-pentyl, hexyl, or cyclohexyl. In particular, a $C_1$–$C_5$ alkyl group is preferred.

The $C_7$–$C_{20}$ aralkyl group may be any suitable one. For example, the $C_7$–$C_{20}$ aralkyl may be benzyl, p-hydroxybenzyl, or p-methoxybenzyl. In particular, a $C_7$–$C_{10}$ aralkyl group is preferred.

The $C_6$–$C_{20}$ aryl group may be any suitable one. For example, the $C_6$–$C_{20}$ aryl group may be phenyl, o-methylphenyl, m-methylphenyl, p-methylphenyl, o-methoxyphenyl, m-methoxyphenyl, p-methoxyphenyl, naphthyl, anthracenyl, 2-furyl, 2-thiophenyl, 2-pyridyl, or 3-pyridyl. In particular, a $C_6$–$C_{10}$ aryl group is preferred.

Preferably, $R^1$ is a t-butyl group.

In formulae (1), (2), (5), and (6) above, $R^2$ represents a $C_1$–$C_{10}$ alkyl group, a $C_7$–$C_{20}$ aralkyl group, or a $C_6$–$C_{20}$ aryl group, each of which may contain a substituent. Examples of the alkyl, aralkyl, and aryl groups and the substituent are the same as those for $R^1$ described above.

In view of easy material preparation and high reaction selectivity in converting to pharmaceutical products or the like after asymmetrical hydrogenation, $R^1$ is preferably a group different from $R^2$. As is previously noted, $R^1$ is preferably butyl and $R^2$ is preferably isopropyl.

In formulae (1), (2), (7), and (8) above, $R^3$s are each independently a $C_1$–$C_{10}$ alkyl group, a $C_7$–$C_{20}$ aralkyl group, or a $C_6$–$C_{20}$ aryl group, or together form a $C_1$–$C_{10}$ alkylene group. The alkyl, aralkyl, aryl, or alkylene group may contain a substituent. Examples of the alkyl group, the aralkyl group, the aryl group, and the substituent are the same as those for $R^1$ described above.

Examples of two R³s forming a $C_1$–$C_{10}$ alkylene group are not particularly limited and include ethylene, propylene, and 2,2-dimethylpropylene. In particular, $C_1$–$C_5$ alkylene group is preferred, and ethylene or propylene is more preferred.

R³ is preferably methyl.

In formulae (1) to (4) above, R⁴ represents a $C_1$–$C_{10}$ alkyl group, a $C_7$–$C_{20}$ aralkyl group, or a $C_6$–$C_{20}$ aryl group, each of which may contain a substituent. Examples of the alkyl group, the aralkyl group, the aryl group, and the substituent are the same as those of R¹ above.

In view of easy material preparation and reaction selectivity in converting to pharmaceutical products or the like after asymmetrical hydrogenation, R¹ is preferably a group different from R⁴. As is previously noted, R¹ is preferably butyl and R⁴ is preferably phenyl.

In formulae (1) to (8) above, "*" represents an asymmetrical carbon atom.

The optically active 3-oxo-5,6-dihydroxyhexanoic acid derivative represented by formula (3) above can be produced, for example, by a method set forth in Japanese Unexamined Patent Application Publication No. 2-262537, including cyanizing a starting material, i.e., an optically active 1-chloro-2,3-propanediol and allowing the resulting product to react with a bromoacetic ester.

The optically active 4-oxo-2-hydroxyadipinic acid derivative represented by formula (5) above can be produced, for example, by a method set forth in Japanese Unexamined Patent Application Publication No. 4-69355, in which a starting material, i.e., an optically active malic acid, is reacted with malonic ester and then transesterified.

The ruthenium-optically active phosphine complex used as the catalyst of the asymmetric hydrogenation of the present invention will now be described. Examples of the ruthenium-optically active phosphine complex include a complex represented by formula (9), a complex represented by formula (10), and a complex represented by formula (11):

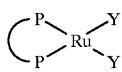
(9)

(wherein

represents an optically active phosphine ligand, Y represents a halogen atom, an acetoxy group, a methylallyl group, or an acetylacetonato group);

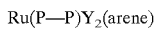 (10)

(wherein P—P represents an optically active phosphine ligand, Y represents a halogen atom, an acetoxy group, a methylallyl group, or an acetylacetonato group, and arene represents an aromatic ligand); and

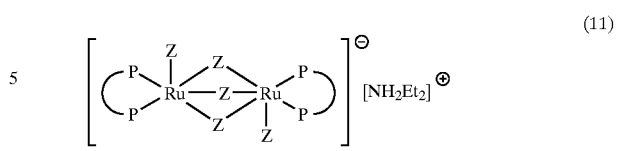 (11)

(wherein

is the same as above, and Z represents a halogen atom).

In formulae (9), (10), and (11) described above, the optically active phosphine ligand is an optically active bisphosphine. Examples thereof include optically active 2,2'-bisdiarylphosphino-1,1'-binaphthyl ("BINAP"), optically active bis(tert-butylmethylphosphino)ethane ("BisP*"), optically active 1,2-bis(trans-2,5-dialkylphosphorano)benzene ("DuPhos"), and optically active 1,2-bis(trans-2,5-dialkylphosphorano)ethane ("BPE"). Optically active 2,2'-bisdiarylphosphino-1,1'-binaphthyl is particularly preferred.

Examples of the aryl group in the optically active 2,2'-bisdiarylphosphino-1,1'-binaphthyl include phenyl, o-methylphenyl, m-methylphenyl, p-methylphenyl, o-methoxyphenyl, m-methoxyphenyl, p-methoxyphenyl, naphthyl, anthracenyl, 2-furyl, 2-thiophenyl, 2-pyridyl, and 3-pyridyl. Phenyl is particularly preferred.

Examples of the alkyl groups in optically active 1,2-bis(trans-2,5-dialkylphosphorano)benzene and optically active 1,2-bis(trans-2,5-dialkylphosphorano)ethane include methyl, ethyl n-propyl, isopropyl, n-butyl, isobutyl, t-butyl, n-pentyl, hexyl, and cyclohexyl. Methyl is particularly preferred.

In formulae (9) and (10) above, Y represents a halogen atom, an acetoxy group, a methylallyl group, or an acetylacetonato group. The halogen atom is preferably iodine, bromine, or chlorine, and more preferably iodine.

In formula (10) above, arene represents an aromatic ligand. Examples of the aromatic ligand are not limited to, but include benzene, toluene, xylene, cumene, cymene, mesitylene, anisole, and naphthalene. Benzene, mesitylene, and cymene are particularly preferred due to the ease of preparing catalysts.

In formula (11) above, Z represents a halogen atom, such as iodine, bromine, or chlorine. In particular, chlorine is preferred.

In order to prepare the ruthenium-optically active phosphine complex represented by formula (9) above, the following methods have been known:

(1) a method in which a widely available [Ru(COD)(methylallyl)₂] (wherein COD represents cycloocta-1,5-diene) is mixed with optically active bisphosphine and the mixture is heated to produce a ruthenium-optically active phosphine complex containing a methylallyl group as Y in formula (9), or this complex is further reacted with a HBr solution to produce a ruthenium-optically active phosphine complex containing a bromine atom as Y in formula (9) (Tetrahedron: Asymmetry, vol. 5, p. 655 (1994));

(2) a method in which [RuCl₂(DOC)]ₙ is reacted with optically active bisphosphine in the presence of triethylamine, and the resulting reaction product is allowed to interact with sodium acetate to produce a ruthenium-optically active phosphine complex containing an acetoxy group as Y in formula (9), or the resulting complex is further mixed with a hydrogen halide aqueous solution to produce a ruthenium-optically active phosphine complex containing a halogen atom as Y in formula (9) (J. Am. Chem. Soc. (1986) vol. 108, p. 7117);

(3) a method in which Ru(acac)$_3$ (wherein acac represents an acetylacetonato group) is reacted with an optically active bisphosphine to produce a ruthenium-optically active phosphine complex having an acetylacetonato group as Y in formula (9) (Organometallics (1993), vol. 12, p. 1467).

In particular, the method of paragraph (1) above is preferred.

The ruthenium-optically active phosphine complex represented by formula (10) described above can be prepared by a conventionally known method in which [RuY$_2$(arene)]$_2$ and optically active bisphosphine are heated in dimethylformamide to produce Ru(P—P)Y$_2$(arene) (J. Org. Chem. vol. 57, p. 4053 (1992)).

The ruthenium-optically active phosphine complex represented by formula (11) described above can be prepared by a conventionally known method in which [RuCl$_2$(COD)]$_n$ is reacted with optically active bisphosphine in the presence of triethylamine (Organometallics (1996), vol. 15, p. 1521).

Among the complexes represented by formulae (9) to (11), the complexes represented by formulae (9) and (10) are particularly preferred as the catalyst for the asymmetric hydrogenation in the present invention since these complexes can render a high stereoselectivity and a high yield and allow hydrogenation under low hydrogen pressure. In particular, the complex represented by formula (9) is more preferred, and the RuBr$_2$BINAP complex is most preferred.

The asymmetric hydrogenation process catalyzed by the ruthenium-optically active phosphine complex will now be explained.

The amount of asymmetric hydrogenation catalyst may be any suitable one as long as the reaction can be sufficiently carried out. The preferable amount of catalyst differs depending on the type of catalyst and solvent, and the conditions of hydrogenation. In view of reaction rate and cost efficiency, the equivalent of the catalyst is preferably 1/50 to 1/100,000 and more preferably 1/100 to 1/10,000 relative to the compound represented by formula (2) above.

During the reaction, the hydrogen pressure is preferably 1 to 100 kg/cm$^2$, and more preferably 1 to 10 kg/cm$^2$.

Examples of the reaction solvent include dichloromethane, chloroform, toluene, benzene, tetrahydrofuran, diethylether, ethyl acetate, N,N-dimethylformamide, formamide, acetone, butanol, isopropanol, ethanol, methanol, and water. These solvents can be used alone or in combination. Preferably, the reaction solvent is water, methanol, or a mixture of methanol and water. More preferably, the reaction solvent is a mixture of methanol and water.

The ratio of methanol to water in the methanol-water mixed solvent described above may be any suitable one but is preferably 100/1 to 1/1, and more preferably 20/1 to 4/1.

For example, reaction may be carried out in the above-described solvent under moderate conditions, i.e., at a reaction temperature in the range of −50° C. to 150° C. The reaction temperature is preferably 0° C. to 60° C. in order to increase the yield. The reaction time is preferably 30 minutes to 24 hours, and more preferably 30 minutes to 20 hours.

Upon completion of the reaction, the resultant reaction mixture is purified by silica gel chromatography or by recrystallization to obtain a target optically active compound.

Best Mode for Carrying out the Invention

The present invention will now be described specifically by way of examples. The present invention is in no way limited by these examples.

EXAMPLE 1

Synthesis of (2S, 4R)-2,4-dihydroxyadipinic acid 1-isopropyl 6-tert-butylester

To (S)-4-oxo-2-hydroxyadipinic acid 1-isopropyl 6-tert-butylester (137 mg, 0.50 mmol) and RuBr$_2$(R)-BINAP (4.4 mg, 0.0050 mmol) (BINAP was 2,2'-bisdiphenylphosphino-1,1'-binaphthyl), 2 mL of a methanol-water (10/1) solution was added to completely dissolve the (S)-4-oxo-2-hydroxyadipinic acid 1-isopropyl 6-tert-butylester and RuBr$_2$(R)-BINAP in an argon atmosphere. Hydrogen replacement at −78° C. was performed three times. After the temperature of the resulting mixture had increased to 50° C., the mixture was allowed to react for three hours under a hydrogen pressure of 5.0 kg/cm$^2$. After extraction of hydrogen, the mixture was condensed and purified by silica gel column chromatography. As a result, 97.8 mg (71%) of (2S, 4R)-2,4-dihydroxyadipinic acid 1-isopropyl 6-tert-butylester was obtained. The diastereomer ratio as determined by nuclear magnetic resonance (NMR) analysis was (2S, 4R):(2S, 4S)=95.5/4.5.

$^1$H-NMR (400 MHz, CDCl$_3$): (2S, 4R) δ1.28 (d, J=6.4 Hz, 6H), 1.46 (s, 9H), 1.80–2.00 (m, 2H), 2.44 (d, J =6.0 Hz, 2H), 3.35 (br, 1H), 3.49 (br, 1H), 4.26–4.41 (m, 2H), 5.09 (sep, J=4.5 Hz, 1H). (2S, 4S,) δ1.28 (d, J=6.4 Hz, 6H), 1.47 (s, 9H), 1.67–1.70 (m, 1H), 1.94–2.10 (m, 1H), 2.43 (d, J=3.6 Hz, 2H), 3.22 (br, 1H), 3.46 (br, 1H), 4.20–4.30 (m, 1H), 4.35–4.50 (m, 1H), 5.11 (sep, J=6.4 Hz, 1H).

EXAMPLE 2

Synthesis of (2S, 4R)-2,4-dihydroxyadipinic acid 1-isopropyl 6-tert-butylester

To (S)-4-oxo-2-hydroxyadipinic acid 1-isopropyl 6-tert-butylester (137 mg, 0.50 mmol) and RuBr$_2$(R)-BINAP (4.4 mg, 0.0050 mmol) (BINAP was 2,2'-bisdiphenylphosphino-1,1'-binaphthyl), 2 mL of a methanol-water (10/1) solution was added to completely dissolve (S)-4-oxo-2-hydroxyadipinic acid 1-isopropyl 6-tert-butylester and RuBr$_2$(R)-BINAP in argon atmosphere. Hydrogen replacement at −78° C. was performed three times. After the temperature of the resulting mixture is increased to 50° C., the mixture was allowed to react for twenty hours under a hydrogen pressure of 5.0 kg/cm$^2$. After extraction of hydrogen, the mixture was condensed and purified by silica gel column chromatography. As a result, 37.9 mg (28%) of (2S, 4R)-2,4-dihydroxyadipinic acid 1-isopropyl 6-tert-butylester was obtained. The diastereomer ratio reported by nuclear magnetic resonance (NMR) analysis was (2S, 4R):(2S, 4S)=94.4/5.6.

EXAMPLE 3

Synthesis of (2S, 4R)-2,4-dihydroxyadipinic acid 1-isopropyl 6-tert-butylester

To (S)-4-oxo-2-hydroxyadipinic acid 1-isopropyl 6-tert-butylester (137 mg, 0.50 mmol) and RuBr$_2$BisP* (2.5 mg, 0.0050 mmol) (BisP* was (S,S)bis(tert-butylmethylphosphino)ethane), 2 mL of a methanol-water (10/1) solution was added to completely dissolve the (S)-4-oxo-2-hydroxyadipinic acid 1-isopropyl 6-tert-butylester and RuBr$_2$BisP* in an argon atmosphere. Hydrogen replacement at −78° C. was performed three times. After the temperature of the resulting mixture had increased to 50° C., the mixture was allowed to react for twenty hours under a hydrogen pressure of 5.0 kg/cm$^2$. After extraction of hydrogen, the mixture was condensed and purified by silica gel column chromatography. As a result, 50.8 mg (37%) of (2S, 4R)-2,4-dihydroxyadipinic acid 1-isopropyl 6-tert-butylester was obtained. The diastereomer ratio determined by nuclear magnetic resonance (NMR) analysis was (2S, 4R):(2S, 4S)=60/40.

EXAMPLE 4

Synthesis of (2S, 4S)-2,4-dihydroxyadipinic acid 1-isopropyl 6-tert-butylester

To (S)-4-oxo-2-hydroxyadipinic acid 1-isopropyl 6-tert-butylester (137 mg, 0.50 mmol) and RuBr$_2$(S)-BINAP (4.4 mg, 0.0050 mmol) (BINAP was 2,2'-bisdiphenylphosphino-1,1'-binaphthyl), 2 mL of a methanol-water (10/1) solution was added to completely dissolve the (S)-4-oxo-2-hydroxyadipinic acid 1-isopropyl 6-tert-butylester and RuBr$_2$(S)-BINAP in an argon atmosphere. Hydrogen replacement at −78° C. was performed three times. After the temperature of the resulting mixture had increased to 50° C., the mixture was allowed to react for twenty hours under a hydrogen pressure of 5.0 kg/cm$^2$. After extraction of hydrogen, the mixture was condensed and purified by silica gel column chromatography. As a result, 46.5 mg (34%) of (2S, 4S)-2,4-dihydroxyadipinic acid 1-isopropyl 6-tert-butylester was obtained. The diastereomer ratio determined by nuclear magnetic resonance (NMR) analysis was (2S, 4R):(2S, 4S)=5.5/94.5.

EXAMPLE 5

Synthesis of (2S, 4S)-2,4-dihydroxyadipinic acid 1-isopropyl 6-tert-butylester

To (S)-4-oxo-2-hydroxyadipinic acid 1-isopropyl 6-tert-butylester (137 mg, 0.50 mmol) and RuBr$_2$(S, S)-Me-DuPhos (2.5 mg, 0.0050 mmol) (Me-DuPhos was 1,2-bis(trans-2,5-dimethylphosphorano)benzene), 2 mL of a methanol-water (10/1) solution was added to completely dissolve the (S)-4-oxo-2-hydroxyadipinic acid 1-isopropyl 6-tert-butylester and RuBr$_2$(S, S)-Me-DuPhos in an argon atmosphere. Hydrogen replacement at −78° C. was performed three times. After the temperature of the resulting mixture had increased to 50° C., the mixture was allowed to react for twenty hours under a hydrogen pressure of 5.0 kg/cm$^2$. After extraction of hydrogen, the mixture was condensed and purified by silica gel column chromatography. As a result, 36.1 mg (26%) of (2S, 4S)-2,4-dihydroxyadipinic acid 1-isopropyl 6-tert-butylester was obtained. The diastereomer ratio determined by nuclear magnetic resonance (NMR) analysis was (2S, 4R):(2S, 4S)=13/87.

EXAMPLE 6

Synthesis of (3R, 5S)-6-benzoyloxy-3,5-dihydroxyhexanoic acid tert-butylester

To (S)-6-benzoyloxy-3-oxo-5-hydroxyhexanoic acid tert-butylester (161 mg, 0.50 mmol) and RuBr$_2$(R)-BINAP (4.4 mg, 0.0050 mmol) (BINAP was 2,2'-bisdiphenylphosphino-1,1'-binaphthyl), 2 mL of a methanol-water (10/1) solution was added to completely dissolve the (S)-6-benzoyloxy-3-oxo-5-hydroxyhexanoic acid tert-butylester and RuBr$_2$(R)-BINAP in an argon atmosphere. Hydrogen replacement at −78° C. was performed three times. After the temperature of the resulting mixture had increased to 50° C., the mixture was allowed to react for twenty hours under a hydrogen pressure of 5.0 kg/cm$^2$. After extraction of hydrogen, the mixture was condensed and purified by silica gel column chromatography. As a result, 144.4 mg (89%) of (3R, 5S)-6-benzoyloxy-3,5-dihydroxyhexanoic acid tert-butylester was obtained. The diastereomer ratio determined by high performance liquid chromatography (HPLC) analysis was (3R, 5S):(3S, 5S)=93.5/6.5 (Chiralcel-AD, hexane/isopropanol=95/5, 1.0 mL/min, UV=210 nm. Retention time: (3R, 5S) 28.2 min, (3S, 5S) 42.9 min).

$^1$H-NMR (500 MHz, CDCl$_3$): (3R, 5S) δ1.47 (s, 9H), 1.68–1.78 (m, 2H), 2.44 (d, J=6.1 Hz, 2H), 3.71 (br, 1H), 3.83 (br, 1H), 4.24–4.36 (m, 4H), 7.43–7.46 (m, 2H), 7.55–7.58 (m, 1H), 8.04–8.08 (m, 2H). (3S, 5S) δ1.47 (s, 9H), 1.73 (t, J=6 Hz, 2H), 2.46 (d, J=7.0 Hz, 2H), 2.99 (br, 1H), 3.57 (br, 1H), 4.25–4.45 (m, 4H), 7.43–7.46 (m, 2H), 7.55–7.59 (m, 1H), 8.04–8.06 (m, 2H).

EXAMPLE 7

Synthesis of (3S, 5S)-6-benzoyloxy-3,5-dihydroxyhexanoic acid tert-butylester

To (S)-6-benzoyloxy-3-oxo-5-hydroxyhexanoic acid tert-butylester (161 mg, 0.50 mmol) and RuBr$_2$(S)-BINAP (4.4 mg, 0.0050 mmol) (BINAP was 2,2'-bisdiphenylphosphino-1,1'-binaphthyl), 2 mL of a methanol-water (10/1) solution was added to completely dissolve the (S)-6-benzoyloxy-3-oxo-5-hydroxyhexanoic acid tert-butylester and RuBr$_2$(S)-BINAP in an argon atmosphere. Hydrogen replacement at −78° C. was performed three times. After the temperature of the resulting mixture had increased to 50° C., the mixture was allowed to react for twenty hours under a hydrogen pressure of 5.0 kg/cm$^2$. After extraction of hydrogen, the mixture was condensed and purified by silica gel column chromatography. As a result, 133.4 mg (82%) of (3S, 5S)-6-benzoyloxy-3,5-dihydroxyhexanoic acid tert-butylester was obtained. The diastereomer ratio determined by high performance liquid chromatography (HPLC) analysis was (3R, 5S):(3S, 5S)=10.4/89.6.

INDUSTRIAL APPLICABILITY

According to the features of the present invention described above, an optically active 3,5-dihydroxyhexanoic acid derivative (1) can be produced by efficiently and cost-effectively reducing an easily synthesizable optically active 3-oxo-5-hydroxyhexanoic acid derivative (2) through asymmetrical hydrogenation catalyzed by a ruthenium-optically active phosphine complex.

What is claimed is:

1. A method for producing an optically active 3,5-dihydroxyhexanoic acid derivative represented by formula (1):

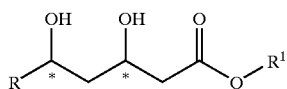
(1)

(wherein $R^1$ is $C_1$–$C_{10}$ alkyl, $C_7$–$C_{20}$ aralkyl, or $C_6$–$C_{20}$ aryl, and R is

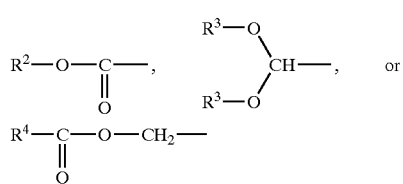

wherein $R^2$ is $C_1$–$C_{10}$ alkyl, $C_7$–$C_{20}$ aralkyl, or $C_6$–$C_{20}$ aryl; $R^3$s are each independently $C_1$–$C_{10}$ alkyl, $C_7$–$C_{20}$ aralkyl, or $C_6$–$C_{20}$ aryl, or together form $C_1$–$C_{10}$ alkylene; and $R^4$ is $C_1$–$C_{10}$ alkyl, $C_7$–$C_{20}$ aralkyl, or $C_6$–$C_{20}$ aryl), the method including a step of conducting asymmetric hydrogenation of an optically active 3-oxo-5-hydroxyhexanoic acid derivative represented by formula (2) in the presence of a ruthenium-optically active phosphine complex as a catalyst:

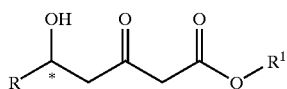
(2)

(wherein R and $R^1$ are the same as described above).

2. The method for producing an optically active 3,5,6-trihydroxyhexanoic acid derivative represented by formula (4)

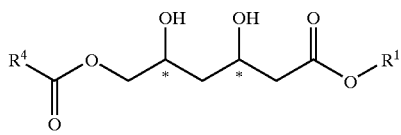
(4)

(wherein $R^1$ and $R^4$ are the same as above) according to claim 1, the method including a step of conducting asymmetric hydrogenation of an optically active 3-oxo-5,6-dihydroxyhexanoic acid derivative represented by formula (3)

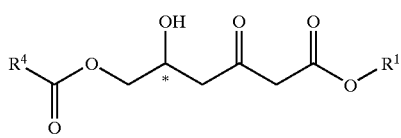
(3)

(wherein $R^1$ and $R^4$ are the same as above).

3. The method for producing an optically active 2,4-dihydroxyadipinic acid derivative represented by formula (6)

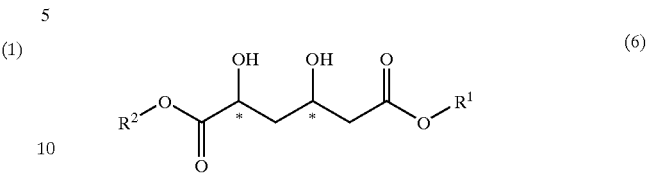
(6)

(wherein $R^1$ and $R^2$ are the same as above) according to claim 1, the method including a step of conducting asymmetric hydrogenation of an optically active 4-oxo-2-hydroxyadipinic acid derivative represented by formula (5)

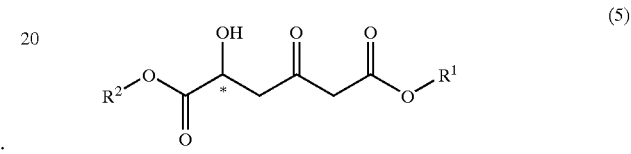
(5)

(wherein $R^1$ and $R^2$ are the same as above).

4. The method for producing an optically active 3,5-dihydroxyhexanoic acid derivative represented by formula (8)

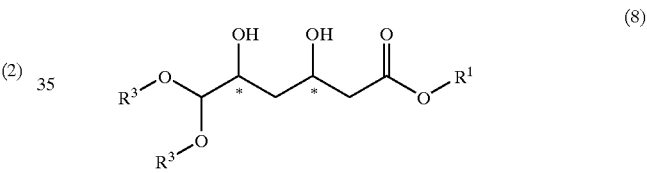
(8)

(wherein $R^1$ and $R^3$ are the same as above) according to claim 1, the method including a step of conducting asymmetric hydrogenation of an optically active 3-oxo-5-hydroxyhexanoic acid derivative represented by formula (7)

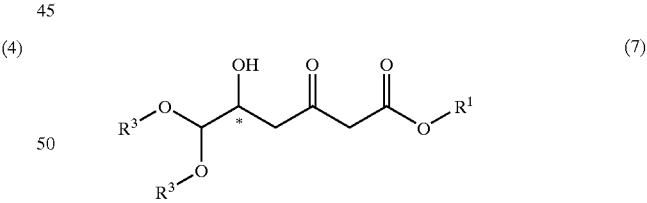
(7)

(wherein $R^1$ and $R^3$ are the same as above).

5. The method according to one of claims 1 to 4, wherein the ruthenium-optically active phosphine complex is one of a complex represented by formula (9), a complex represented by formula (10), and a complex represented by formula (11)

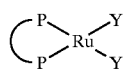
(9)

(wherein

represents an optically active phosphine ligand, Y represents a halogen atom, an acetoxy group, a methylallyl group, or an acetylacetonato group);

$$Ru(P\!-\!P)Y_2(arene) \quad (10)$$

(wherein P—P represents an optically active phosphine ligand, Y represents a halogen atom, an acetoxy group, a methylallyl group, or an acetylacetonato group, and arene represents an aromatic ligand); and

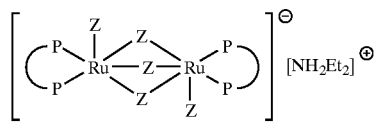 (11)

(wherein

is the same as above, and Z represents a halogen atom).

6. The method according to claim 5, wherein the optically active phosphine ligand is optically active 2,2 '-bisdiarylphosphino-1,1'-binaphthyl (BINAP), optically active bis(tert-butylmethylphosphino)ethane (BisP*), optically active 1,2-bis (trans-2,5-dialkylphosphorano)benzene (DuPhos), or optically active 1,2-bis(trans-2,5-dialkylphosphorano)ethane (BPE).

7. The method according to claim 6, wherein the optically active phosphine ligand is 2,2'-bisdiarylphosphino-1,1'-binaphthyl (BINAP).

8. The method according to claim 5, wherein the ruthenium-optically active phosphine complex is the complex represented by formula (9) containing a bromine atom as Y.

9. The method according to claim 5, wherein the ruthenium-optically active phosphine complex is a $RuBr_2BINAP$ complex, in which the optically active phosphine ligand is 2,2'-bisdiarylphosphino-1,1'-binaphthyl (BINAP) and Y is a bromine atom.

10. The method according to claim 5, wherein the asymmetric hydrogenation is conducted at a hydrogen pressure of 1 to 10 kg/cm2.

11. The method according to claim 5, wherein the asymmetric hydrogenation is conducted at a reaction temperature in the range of from 0 to 60° C.

12. The method according to claim 5, wherein the reaction solvent is a methanol-water mixed solvent.

* * * * *